US009877696B2

(12) United States Patent
Taki

(10) Patent No.: US 9,877,696 B2
(45) Date of Patent: Jan. 30, 2018

(54) RADIOGRAPHIC IMAGE PROCESSING APPARATUS AND METHOD AND RECORDING MEDIUM STORING THEREIN RADIOGRAPHIC IMAGE PROCESSING PROGRAM

(71) Applicant: FUJIFILM Corporation, Tokyo (JP)

(72) Inventor: Tomoko Taki, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/254,516

(22) Filed: Sep. 1, 2016

(65) Prior Publication Data

US 2017/0065244 A1   Mar. 9, 2017

(30) Foreign Application Priority Data

Sep. 9, 2015   (JP) ................................ 2015-177189

(51) Int. Cl.
*G06K 9/00* (2006.01)
*A61B 6/00* (2006.01)

(52) U.S. Cl.
CPC ............ *A61B 6/544* (2013.01); *A61B 6/4291* (2013.01); *A61B 6/5258* (2013.01); *A61B 6/545* (2013.01); *A61B 6/502* (2013.01)

(58) Field of Classification Search
None
See application file for complete search history.

(56) References Cited

U.S. PATENT DOCUMENTS

| | | | |
|---|---|---|---|
| 7,386,158 B2 | 6/2008 | Yamada | |
| 2007/0071172 A1* | 3/2007 | Mollus | A61B 6/00 378/108 |
| 2010/0322375 A1* | 12/2010 | Hirokawa | A61B 6/032 378/4 |
| 2011/0026668 A1* | 2/2011 | Wu | A61B 6/032 378/16 |
| 2013/0251093 A1* | 9/2013 | Akino | A61B 6/032 378/4 |
| 2014/0005533 A1* | 1/2014 | Grasruck | A61B 6/032 600/425 |

(Continued)

FOREIGN PATENT DOCUMENTS

| | | |
|---|---|---|
| JP | 2003-284713 A | 10/2003 |
| JP | 2010-5252 A | 1/2010 |
| JP | 2011-239804 A | 12/2011 |

*Primary Examiner* — Atiba O Fitzpatrick
(74) *Attorney, Agent, or Firm* — Sughrue Mion, PLLC

(57) ABSTRACT

An image obtainment unit obtains a radiographic image radiographed by irradiating a subject with radiation. A first information obtainment unit obtains information about at least one of a radiography condition during radiography of the subject, a subject condition and detector characteristics, which are characteristics of the radiation detector. A second information obtainment unit obtains body thickness information representing the body thickness of the subject. A target S/N setting unit sets a target S/N of the radiographic image based on the body thickness information and the information about at least one of the radiography condition, the subject condition and the detector characteristics. An image processing unit corrects the S/N of the radiographic image to the target S/N by performing, on the radiographic image, noise removal processing.

12 Claims, 6 Drawing Sheets

(56) References Cited

U.S. PATENT DOCUMENTS

| | | | |
|---|---|---|---|
| 2014/0153803 A1* | 6/2014 | Noda | G06T 7/0012 |
| | | | 382/131 |
| 2015/0297165 A1* | 10/2015 | Tanaka | A61B 6/032 |
| | | | 378/4 |
| 2016/0086328 A1* | 3/2016 | Enomoto | G06T 11/60 |
| | | | 382/132 |
| 2016/0157794 A1* | 6/2016 | Gibson | A61B 6/032 |
| | | | 378/62 |

* cited by examiner

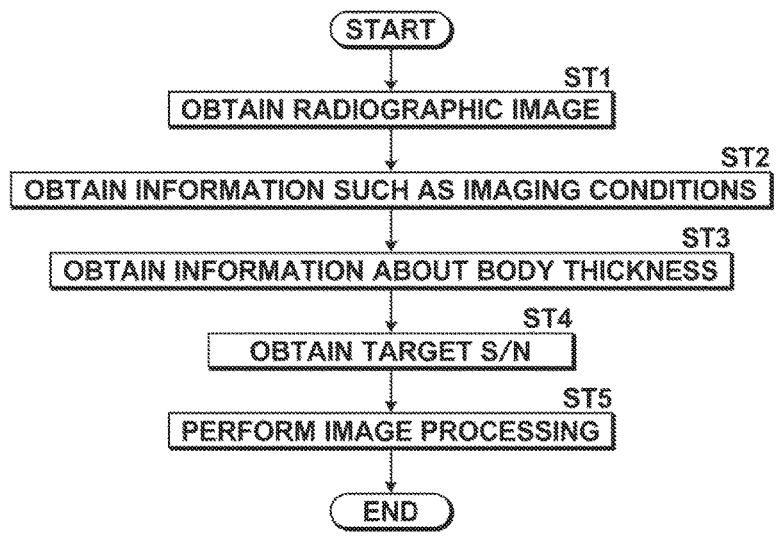

RADIOGRAPHIC IMAGE PROCESSING APPARATUS AND METHOD AND RECORDING MEDIUM STORING THEREIN RADIOGRAPHIC IMAGE PROCESSING PROGRAM

CROSS-REFERENCE TO RELATED APPLICATION

The present application claims priority under 35 U.S.C. §119 to Japanese Patent Application No. 2015-177189, filed on Sep. 9, 2015. The above application is hereby expressly incorporated by reference, in its entirety, into the present application.

BACKGROUND

The present disclosure relates to a radiographic image processing apparatus, method and program for performing noise removal processing on a radiographic image.

Conventionally, in diagnosis using radiographic images of a subject, the radiographic images are displayed on a display device, such as a liquid crystal monitor, or output on a film as a hard copy after various kinds of image processing are performed on radiographic images obtained by radiography to make the radiographic images suitable for diagnosis. Here, radiographic images have a problem that noise, such as quantum noise of radiation, is noticeable in a low density area, in which a radiation dose is low. Therefore, as image processing for radiographic images, various methods for performing noise removal processing for suppressing or removing noise included in the radiographic images have been proposed. Further, various methods for improving the image quality of radiographic images by changing the contrast of the radiographic images have also been proposed.

Incidentally, noise included in a radiographic image and the contrast of the radiographic image vary depending on a radiography condition, a subject condition and detector characteristics, which are the characteristics of a detector for detecting radiation that has passed through a subject. Therefore, image processing is performed on the radiographic image based on the radiography condition, the subject condition and the detector characteristics. Accordingly, a high-image-quality radiographic image, in which noise has been appropriately removed and the contrast has been adjusted based on the radiography condition, the subject condition and the detector characteristics, is obtainable.

Meanwhile, while a radiographic image of a subject is radiographed, especially if the thickness of the subject is large, the amount of primary radiation, which passes through the subject without scatter within the subject and is detected by a radiation detector, is small. Further, the energy of radiation that has passed through the subject becomes relatively high. Therefore, the ratio of scattered radiation becomes high, and noise is more noticeable than signal values. Further, if the thickness of the subject is large, the amount of scattered radiation (hereinafter, referred to as "scattered radiation"), which is radiation that has scattered within the subject, becomes large, and the contrast of an obtained radiographic image becomes lower. Therefore, various kinds of techniques for changing the degree of image processing based on the thickness of a subject have been proposed. For example, Japanese Unexamined Patent Publication No. 2003-284713 (Patent Document 1) proposes a technique for lowering parameters of a contrast and frequency emphasis processing if a body thickness, which is the thickness of a subject, is small, and increasing these parameters if the body thickness is large. Further, Japanese Unexamined Patent Publication No. 2011-239804 (Patent Document 2) proposes a technique for performing noise removal processing and contrast emphasis processing based on a body thickness. Japanese Unexamined Patent Publication No. 2010-005252 (Patent Document 3) proposes a technique for performing image processing so that a bone region included in a radiographic image is emphasized as a body thickness is larger.

SUMMARY

Noise included in a radiographic image is removable based on a body thickness by using the techniques disclosed in Patent Document 1 through 3. However, signal values and noise included in a radiographic image vary depending on a radiography condition, a subject condition and detector characteristics, and a signal to noise ratio, i.e., S/N of the radiographic image differs. Therefore, if noise is removed from a radiographic image while only a body thickness is taken into consideration, a. radiographic image having an appropriate S/N is not obtainable.

In view of the foregoing circumstances, the present disclosure is directed to obtain a radiographic image having an appropriate S/N based on a radiography condition or the like while the body thickness of a subject is taken into consideration.

A radiographic image processing apparatus of the present disclosure includes an image obtainment means that obtains a radiographic image radiographed by irradiating a subject with radiation and by detecting the radiation passed through the subject by a radiation detector, a first information obtainment means that obtains information about at least one of a radiography condition during radiography of the subject, a subject condition and detector characteristics, which are characteristics of the radiation detector, a second information obtainment means that obtains body thickness information representing the body thickness of the subject, a target S/N setting means that sets a target S/N of the radiographic image based on the body thickness information and information about at least one of the radiography condition, the subject condition and the detector characteristics, and an image processing means that corrects the S/N of the radiographic image to the target S/N by performing, on the radiographic image, noise removal processing for removing noise.

The term "body thickness" means the total thickness of a subject region, which excludes an air region, on the path of radiation with which a subject is irradiated.

In the radiographic image processing apparatus of the present disclosure, the image processing means may increase the degree of removal of noise included in the radiographic image as the body thickness is larger.

Further, in the radiographic image processing apparatus of the present disclosure, the image processing means may increase the degree of removal of noise by increasing the degree of a blur of the radiographic image as the body thickness is larger.

Further, in the radiographic image processing apparatus of the present disclosure, the target S/N setting means may set the target S/N lower as the body thickness is larger.

In the radiographic image processing apparatus of the present disclosure, the image processing means may further perform contrast adjustment processing on the radiographic image.

In this case, the contrast of the radiographic image may be adjusted based on the degree of removal of the noise.

The term "contrast" means a difference in grayscale or density in a radiographic image with respect to tissues included in a subject, and which have different radiation absorption ratios from each other. For example, in the case that the subject is a breast, the breast includes a mammary gland and fat, which have different radiation absorption ratios from each other. Further, radiation absorption ratios of tissues constituting the mammary gland differ from each other. Therefore, in the case that the subject is a breast, the term "contrast" means a difference in grayscale or density between a mammary gland and fat in a radiographic image, and further a difference in grayscale or density between different tissues constituting the mammary gland.

Further, in the radiographic image processing apparatus of the present disclosure, the image processing means may perform the noise removal processing by separating a noise component included in the radiographic image from the radiographic image, and by suppressing the separated noise component. In the case that contrast adjustment processing is further performed, the contrast adjustment processing may be performed by adjusting the contrast of the radiographic image from which the noise component has been separated.

In the radiographic image processing apparatus of the present disclosure, the image processing means may perform the noise removal processing by generating band images of a plurality of frequency bands by decomposing the radiographic image into the plurality of frequency bands, and by suppressing a band image of a frequency band corresponding to noise. In the case that contrast adjustment processing is further performed, the contrast adjustment processing may be performed by adjusting the contrast of a band image of a frequency band corresponding to density information about the radiographic image.

A radiographic image processing method of the present disclosure includes obtaining a radiographic image radiographed by irradiating a subject with radiation and by detecting the radiation passed through the subject by a radiation detector, obtaining information about at least one of a radiography condition during radiography of the subject, a subject condition and detector characteristics, which are characteristics of the radiation detector, obtaining body thickness information representing the body thickness of the subject, setting a target S/N of the radiographic image based on the body thickness information and information about at least one of the radiography condition, the subject condition and the detector characteristics, and correcting the S/N of the radiographic image to the target S/N by performing, on the radiographic image, noise removal processing for removing noise.

According to the present disclosure, a target S/N of a radiographic image is set based on information about at least one of a radiography condition, a subject condition and detector characteristics and body thickness information, and an S/N of the radiographic image is corrected to the target S/N by performing noise removal processing on the radiographic image. Therefore, a high-image-quality radiographic image having an appropriate S/N based on the body thickness information and information about at least one of the radiography condition, the subject condition and the detector characteristics is obtainable.

BRIEF DESCRIPTION OF THE DRAWINGS

FIG. 15 is a flow chart showing processing performed in embodiments of the present disclosure.

DETAILED DESCRIPTION OF THE PREFERRED EMBODIMENTS

Figure 1:
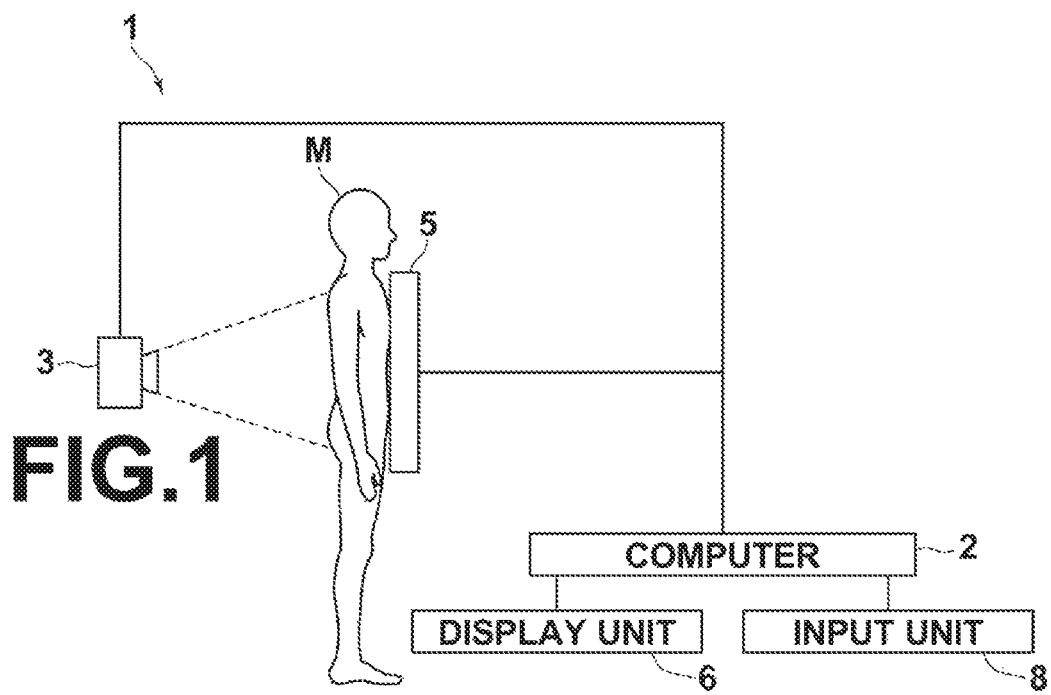
FIG. 1 is a schematic block diagram illustrating the configuration of a radiography system to which a radiographic image processing apparatus according to embodiments of the present disclosure has been applied.

Hereinafter, embodiments of the present disclosure will be described with reference to drawings. FIG. 1 is a schematic block diagram illustrating the configuration of a radiography system to which a radiographic image processing apparatus according to an embodiment of the present disclosure has been applied. As illustrated in FIG. 1, a radiography system according to the present embodiment is a system for radiographing a radiographic image of subject M, and performing, on the radiographic image, various kinds of image processing including noise removal processing for suppressing or removing quantum noise (hereinafter, simply referred to as "noise") included in the radiographic image. The radiography system includes a radiography apparatus 1 and a computer 2 including a radiographic image processing apparatus according to the present embodiment.

The radiography apparatus 1 includes an X-ray source 3 that irradiates subject M with X-rays, which are radiation, and a radiation detector 5 that obtains radiographic image G0 of subject M by detecting X-rays that have passed through subject M.

The radiation detector 5 is able to repeatedly record radiographic images therein and the radiographic images are able to be repeatedly read out therefrom. So-called direct-type radiation detector, which generates charges by directly receiving radiation, may be used, or a so-called indirect-type radiation detector, which temporarily converts radiation into visible light and converts the visible light into charge signals, may be used. As methods for reading out radiographic image signals, it is desirable to use a so-called TFT (thin film transistor) readout method, in which radiographic image signals are read out by on/off of a TFT switch, or a so-called light readout method, in which radiographic image signals are read out by irradiation with readout light. However, the method is not limited to these methods, and other methods are adoptable.

A display unit 6 and an input unit 8 are connected to the computer 2. The display unit 6 includes a CRT (Cathode Ray Tube), a liquid crystal display, or the like, and displays a radiographic image obtained by radiography, and assists various kinds of input necessary for processing performed in the computer 2. The input unit 8 includes a keyboard, a mouse, a touch panel or the like.

A radiographic image processing program of the present embodiment has been installed in the computer 2. In the present embodiment, the computer may be a workstation or a personal computer directly operated by an operator, or a server computer connected to them through a network. The radiographic image processing program is recorded in a recording medium, such as a DVD (Digital Versatile Disc) and a CD-ROM (Compact Disc Read Only Memory), and distributed, and installed in a computer from the recording medium Alternatively, the radiographic image processing program is recorded in a storage device of a server computer connected to a network, or a network storage in an accessible manner from the outside, and downloaded in a computer based on a request, and installed in the computer.

Figure 2:
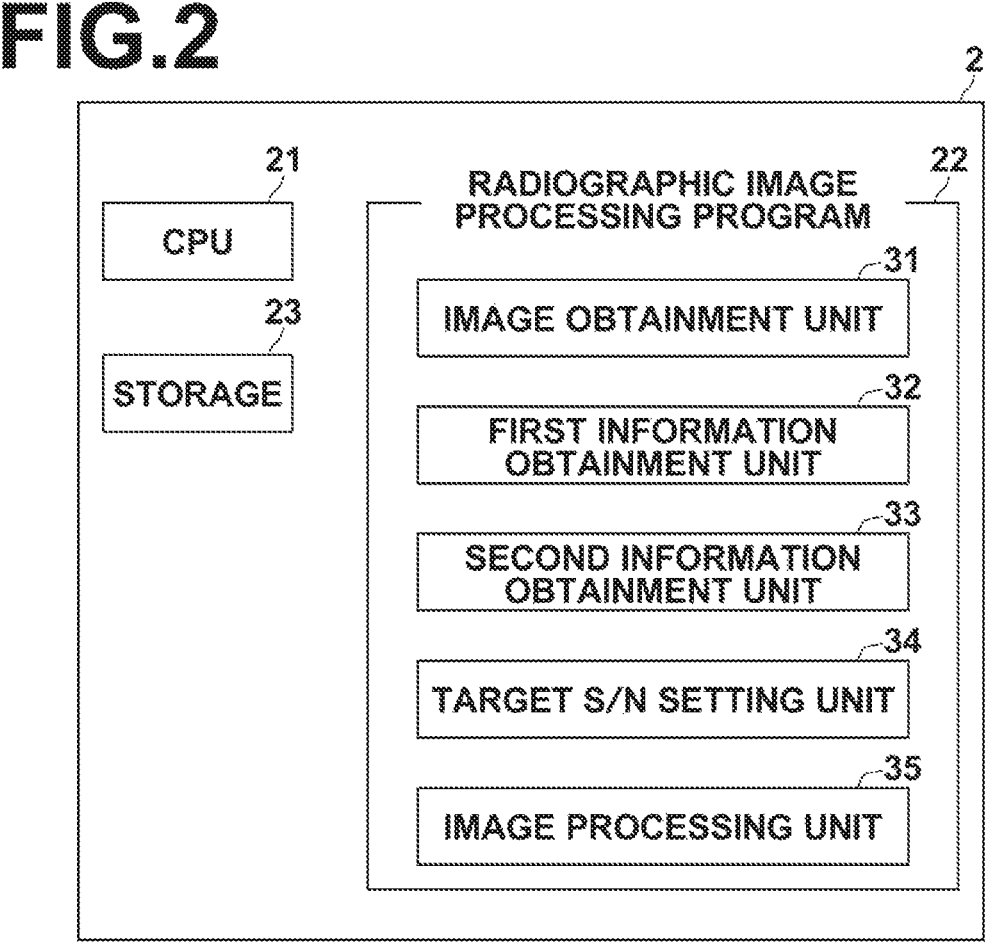
FIG. 2 is a schematic diagram illustrating the configuration of a radiographic image processing apparatus embodied by installing a radiographic image processing program in a computer.

FIG. 2 is a schematic diagram illustrating the configuration of a radiographic image processing apparatus embodied by installing a radiographic image processing program in the computer 2. As illustrated in FIG. 2, the radiographic image processing apparatus includes a CPU (Central Processing Unit) 21, a memory 22 and a storage 23, as standard computer configuration.

The storage 23 includes a storage device, such as a hard disk or an SSD (Solid State Drive), and various kinds of information including a program for driving each unit of the radiography apparatus 1 and a radiographic image processing program are stored in the storage 23. Further, a radiographic image obtained by radiography is also stored in the storage 23. Further, various kinds of table that will be described later are also stored in the storage 23.

The program or the like stored in the storage 23 is temporarily stored in the memory 22 to cause the CPU 21 to execute various kinds of processing. The radiographic image processing program defines, as processing to be executed by the CPU 21, image obtainment processing that obtains radiographic image G0 of subject M by causing the radiography apparatus 1 to perform radiography, first information obtainment processing that obtains information about at least one of a radiography condition during radiography of subject M, a subject condition and detector characteristics, which are characteristics of the radiation detector 5, second information obtainment processing that obtains body thickness information representing the body thickness of subject M, target S/N setting processing that sets a target S/N of radiographic image G0 based on the body thickness information and information about at least one of the radiography condition, the subject condition and the detector characteristics, and image processing that corrects the S/N of radiographic image G0 to the target S/N by performing, on radiographic image G0, noise removal processing.

Further, the computer 2 functions as an image obtainment unit 31, a first information obtainment unit 32, a second information obtainment unit 33, a target S/N setting unit 34, and an image processing unit 35 by execution of these kinds of processing by the CPU 21 based on the radiographic image processing program. Here, the computer 2 may include processors for performing image obtainment processing, first information obtainment processing, second information obtainment processing, target S/N setting processing, and image processing, respectively.

The image obtainment unit 31 obtains a radiographic image of subject M by performing radiography on subject M. Specifically, the image obtainment unit 31 obtains radiographic image G0 of subject M by irradiating subject M with X-rays by driving the X-ray source 3, and by detecting X-rays that have passed through subject M by the radiation detector 5. Here, radiographic image G0 may be obtained by a program separate from the radiographic image processing program, and stored in the storage 23. In this case, the image obtainment unit 31 reads out radiographic image G0 stored in the storage 23 to perform image processing on radiographic image G0.

The first information obtainment unit 32 obtains information about at least one of a radiography condition during radiography of subject M, a subject condition and detector characteristics, which are characteristics of the radiation detector 5. Here, the radiography condition and the subject condition are set by input at the input unit 8 by an operator at the time of radiography, and stored in the storage 23. Therefore, the first information obtainment unit 32 obtains the radiography condition and subject condition from the storage 23. Here, the radiography condition may be input from the radiography apparatus 1, and stored in the storage 23. Further, a subject condition may be generated by an analysis apparatus, which is not illustrated, by analyzing radiographic image G0 obtained by radiography, and the generated subject condition may be stored in the storage 23.

Further, the detector characteristics have been determined based on the kind of the radiation detector 5 to be used. In the present embodiment, a table showing detector characteristics based on the kind of the radiation detector 5 is stored in the storage 23. The first information obtainment unit 32 receives an input of the kind of the radiation detector 5 to be used, for example, such as an ID of the radiation detector 5 at the input unit 8 by an operator, and obtains detector characteristics based on the kind of the radiation detector 5 to be used by referring to the table showing detector characteristics based on the kind of the radiation detector 5.

The second information obtainment unit 33 obtains body thickness information representing the body thickness of subject M. In the present embodiment, the operator measures the body thickness of subject M. Further, the second information obtainment unit 33 obtains body thickness information by receiving an input of a result of measuring the body thickness to the computer 2 at the input unit 8 by the operator. Here, a distance measurement apparatus, such as an ultrasonic distance meter, may he provided in the radiography apparatus 1, and distance L1 between the X-ray source 3 and a detection surface of the radiation detector 5 and distance L2 between the X-ray source 3 and a surface of subject M may be measured and the results of measurement may be input to the computer 2 from the distance measurement apparatus. Further, the second information obtainment unit 33 may obtain body thickness information by calculating a difference between distance L1 and distance L2.

Alternatively, body thickness information about subject M may be obtained by analyzing the radiographic image. In this case, the second information obtainment unit 33 generates, based on an imaginary model of subject M having initial body thickness distribution (predetermined body thickness distribution), a combined image of an estimated primary radiation image, which has estimated a primary radiation image obtained by X-ray radiography of the imaginary model, and an estimated scattered radiation image, which has estimated a scattered radiation image obtained by X-ray radiography of the imaginary model, as an estimated image that estimates a radiographic image obtained by X-ray radiography of subject M. Further, the second information obtainment unit 33 obtains the body thickness of subject M by correcting, based on the estimated image and radiographic image G0, the initial body thickness distribution of the imaginary model so that a difference between the estimated image and radiographic image G0 becomes small. In this case, the body thickness is obtained at each pixel position on subject M included in radiographic image G0. Therefore, the body thickness information is obtained by averaging the body thickness obtained at each pixel position, or the like.

The target S/N setting unit 34 sets a target S/N of radiographic image G0 based on the body thickness information and information about at least one of the radiography condition, the subject condition and the detector characteristics. Here, if at least one of the radiography condition, the subject condition and the detector characteristics varies, the S/N of radiographic image G0 changes. Further, in the case that the body thickness of subject M varies, the S/N of radiographic image G0 also changes. For example, the ratio of primary radiation that has passed through subject M is smaller and the ratio of scattered radiation is larger as the body thickness is larger. Therefore, noise becomes more noticeable in radiographic image G0, and the S/N becomes lower.

In the present embodiment, tables defining relationships between body thicknesses and target S/N's based on various kinds of radiography condition, tables defining relationships between body thicknesses and target S/N's based on various kinds of subject condition, and tables defining relationships between body thicknesses and target S/N's based on various kinds of detector characteristics are stored in the storage 23. Next, the relationships between body thicknesses and target S/N's based on the radiography condition, the subject condition and the detector characteristics will be described.

Figure 3:
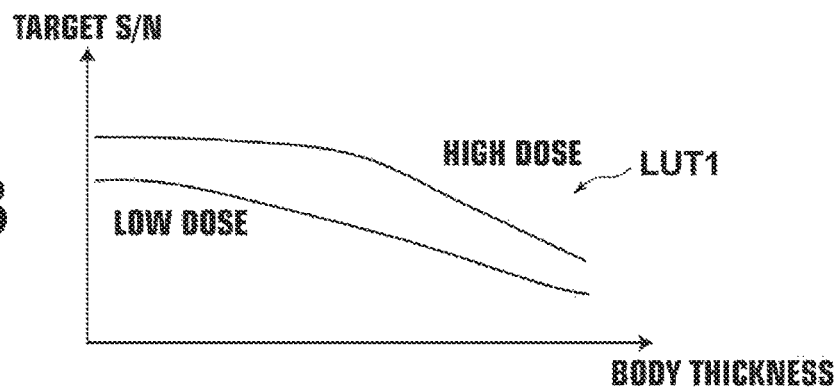
FIG. 3 is a diagram illustrating a table defining relationships between body thicknesses and target S/N's based on a dose.

The radiography condition includes a dose, a radiation quality, whether a grid for removing scattered radiation is present or not, the kind of the grid and the like, as elements constituting the radiography condition. Regarding the dose, noise is more noticeable as the dose is smaller, and an S/N, which is the ratio of signal to noise, of a radiographic image becomes lower. FIG. 3 is a diagram illustrating a table defining relationships between body thicknesses and target S/N's based on a dose. In FIG. 3 and FIG. 4 through FIG. 13, which will be described next, tables LUT1 through LUT11 define the body thickness on the horizontal axis, and the target S/N: on the vertical axis. Further, the relationships between the body thicknesses and the target S/N's based on respective elements are defined. In table LUT1 illustrated in FIG. 3, the target S/N is lower as the dose is smaller, and as the body thickness is larger. In FIG. 3 through FIG. 13 except FIG. 6, the relationships between body thicknesses and target S/N's at the maximum value and the minimum value of each element are illustrated. Therefore, in the case that the value of an element is a value between the maximum value and the minimum value, the target S/N is set by referring to a value between the maximum value and the minimum value shown in each table.

Figure 4:
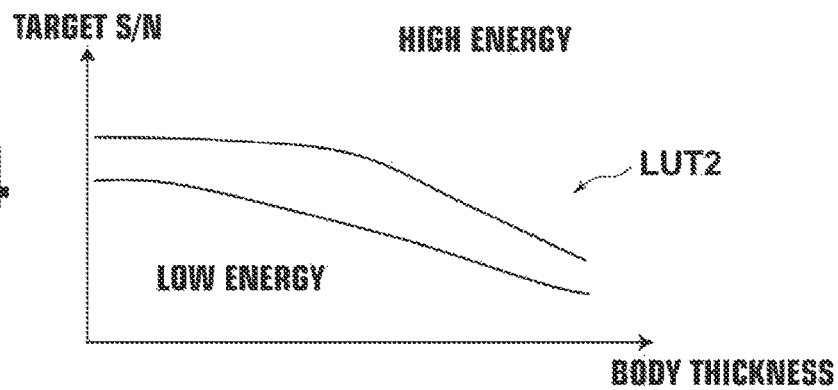
FIG. 4 is a diagram illustrating a table defining relationships between body thicknesses and target S/N's based on X-ray energy.

Regarding the radiation quality, X-ray energy varies based on the tube voltage of the X-rays source 3 and the kind of a target and a filter. Here, the dose of X-rays that pass through subject M becomes larger as the X-ray energy is higher. Therefore, the S/N becomes higher. FIG. 4 is a diagram illustrating a table defining relationships between body thicknesses and target S/N's based on the radiation quality. In table LUT2, illustrated in FIG. 4, the target S/N is lower as the radiation quality is lower energy, and as the body thickness is larger.

Figure 5:
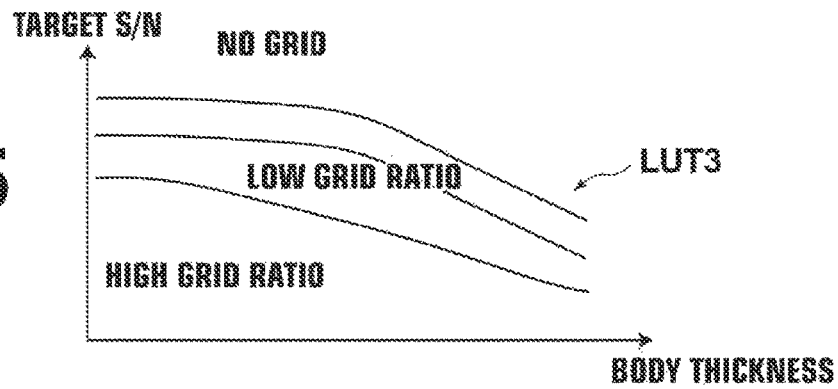
FIG. 5 is a diagram illustrating a table defining relationships between body thicknesses and target S/N's based on a grid ratio.

Regarding the grid for removing scattered radiation that has passed through subject M, the dose of X-rays that have passed through subject M, and the scattered radiation of which has been removed by the grid, is larger as the grid ratio is lower. Therefore, the S/N is higher. FIG. 5 is a diagram illustrating a table defining relationships between body thicknesses and target S/N's based on a grid ratio. In FIG. 5, target S/N's for body thicknesses in the case that no grid is provided are also illustrated. In table LUT3, illustrated in FIG. 5, the target S/N is lower as the grid ratio is higher, and as the body thickness is larger.

Figure 6:
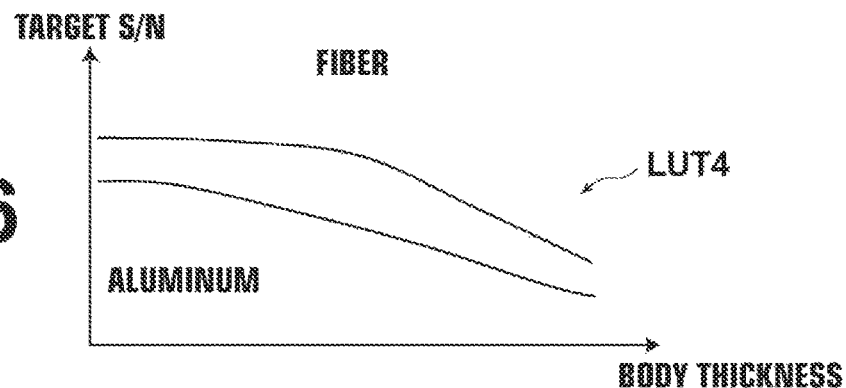
FIG. 6 is a diagram illustrating a table defining relationships between body thicknesses and target S/N's based on the kind of interspace material constituting a grid.

Here, lead, which blocks X-rays, and interspace material that passes X-rays are alternately arranged to constitute the grid. Regarding the kind of the grid, the kind of the interspace material constituting the grid may be given. Regarding the interspace material constituting the grid, the transmittance of primary radiation in the case that the interspace material is fiber is higher than the transmittance of primary radiation in the case that the interspace material is aluminum. Meanwhile, the transmittance of scattered radiation does not vary depending on the interspace material. Therefore, the S/N is higher in the case that the interspace material is fiber. FIG. 6 is a diagram illustrating a table defining relationships between body thicknesses and target S/N's based on the kind of interspace material constituting a grid. In FIG. 6, the relationships between body thicknesses and target SN's are illustrated for aluminum and fiber, as the interspace material. In table LUT4, illustrated in FIG. 6, the target S/N is lower as the body thickness is larger for both of the case in which the interspace material is aluminum and the case in which the interspace material is fiber. Further, the target S/N is lower in the case that the interspace material is aluminum.

Figure 7:
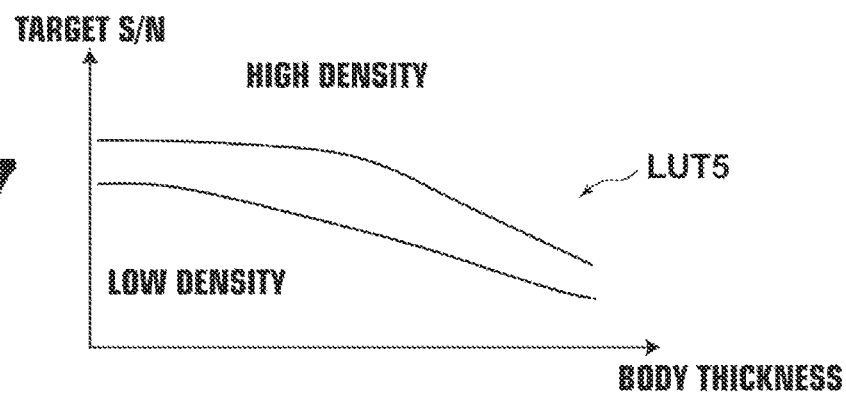
FIG. 7 is a diagram illustrating a table defining relationships between body thicknesses and target S/N's based on the density of a subject.

The subject condition includes density based on the composition of subject M and the amount of structure based on the composition, as elements constituting the subject condition. Regarding the density based on the composition of subject M, noise is more noticeable in a low density region, such as bone and a mammary gland. Therefore, the S/N is lower. FIG. 7 is a diagram illustrating a table defining relationships between body thicknesses and target S/N's based on the density of a subject. In table LUT5, illustrated in FIG. 7, the target S/N is lower as the subject has lower density, and as the body thickness is larger.

Figure 8:
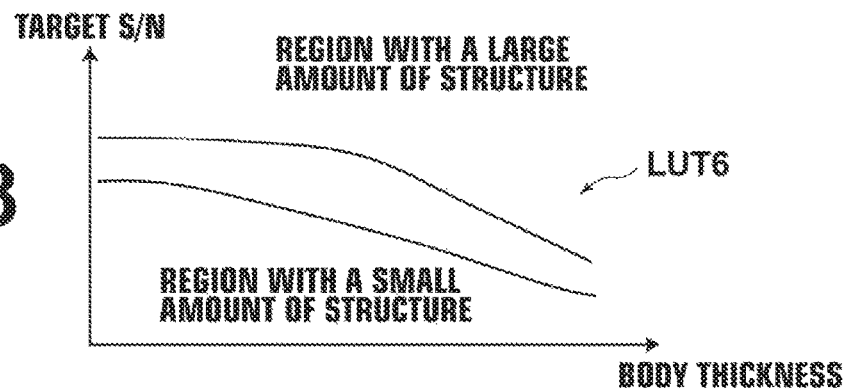
FIG. 8 is a diagram illustrating a table defining relationships between body thicknesses and target S/N's based on the amount of structure included in a subject.

Regarding the amount of structure based on composition, a fat region includes less structure, and is often a region having uniform density. Therefore, the S/N is lower than a region including more structure. FIG. 8 is a diagram illustrating a table defining relationships between body thicknesses and target S/N's based on the amount of structure included in a subject. In table LUT6 illustrated in FIG. 8, the target S/N is lower as the structure is less, and as the body thickness is larger.

Figure 9:
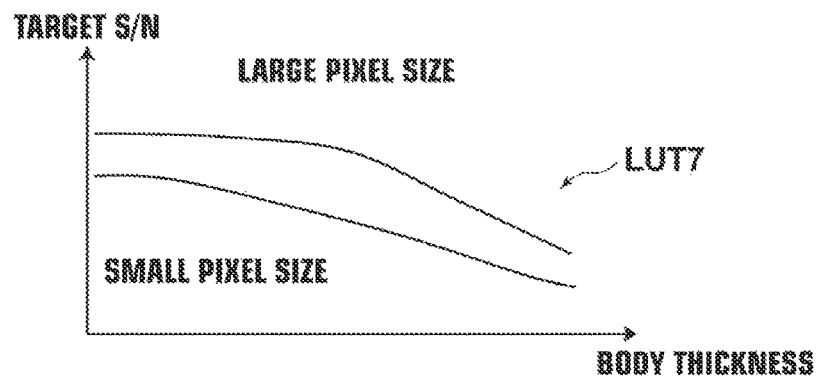
FIG. 9 is a diagram illustrating a table defining relationships between body thicknesses and target S/N's based on the pixel size of a radiation detector.

The detector characteristics include the sharpness of the radiation detector 5, X-ray absorption characteristics, scintillation characteristics and the film thickness of a scintillator for converting X-rays into visible light, as elements constituting the detector characteristics. Regarding the sharpness, noise increases as the sharpness of high frequency is higher. Therefore, the S/N is lower. As elements affecting the sharpness, the pixel size of the radiation detector 5, whether the energy of irradiating X-rays is high or low, and the film thickness of a scintillator may be given. Regarding the pixel size, the sharpness is lower as the pixel size is larger. Therefore, the S/N is higher. FIG. 9 is a diagram illustrating a table defining relationships between body thicknesses and target S/N's based on the pixel size of the radiation detector 5. In table LUT7, illustrated in FIG. 9, the target S/N is lower as the pixel size is smaller, and as the body thickness is larger.

Regarding whether the X-ray energy is high or low, the sharpness is lower as the energy of X-rays irradiating subject M is higher. Therefore, the S/N is higher. In this case, a table defining relationships between body thicknesses and target S/N's based on the X-ray energy is the same as table LUT2, illustrated in FIG. 4.

Figure 10:
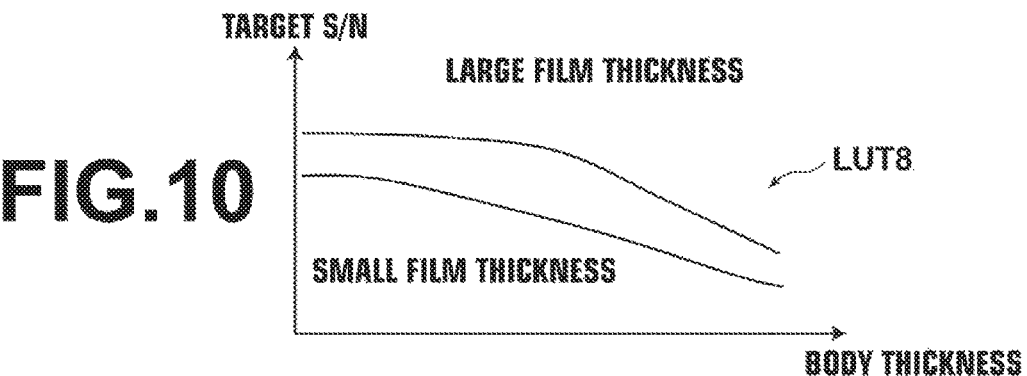
FIG. 10 is a diagram illustrating a table defining relationships between body thicknesses and target S/N's based on the film thickness of a scintillator of a radiation detector.

Regarding the film thickness of the scintillator of the radiation detector 5, the sharpness is lower as the film thickness is larger. Therefore, the S/N is higher. FIG. 10 is a diagram illustrating a table defining relationships between body thicknesses and target S/N's based on the film thickness of the scintillator of the radiation detector 5. In table LUT8, illustrated in FIG. 10, the target S/N is lower as the film thickness of the scintillator is smaller, and as the body thickness is larger.

Figure 11:
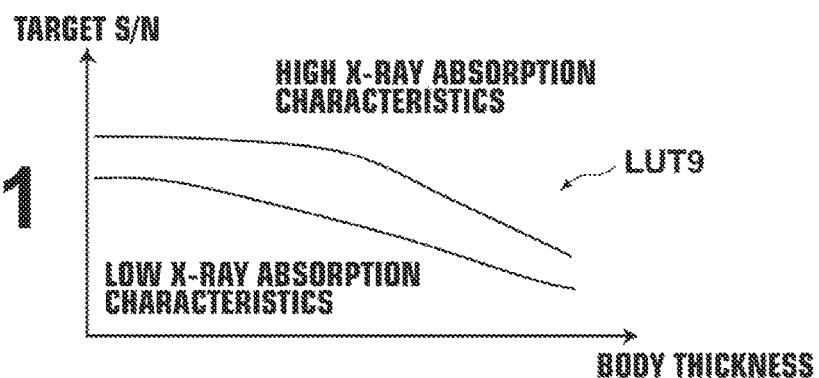
FIG. 11 is a diagram illustrating a table defining relationships between body thicknesses and target S/N's based on the X-ray absorption characteristics of a radiation detector.
Figure 12:
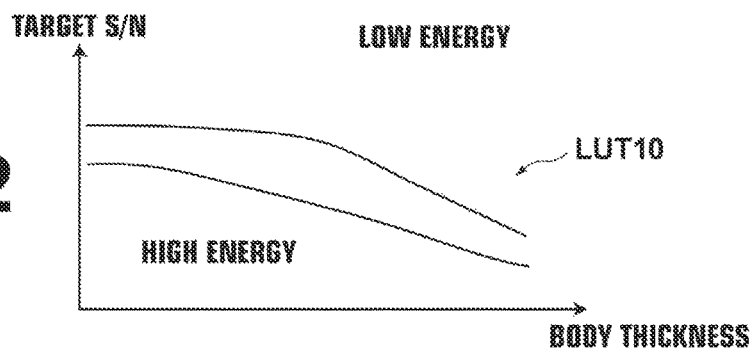
FIG. 12 is a diagram illustrating a table defining relationships between body thicknesses and target S/N's based on X-ray energy with respect to the kind of a scintillator of a radiation detector.

Regarding the X-ray absorption characteristics, signal values are larger as the X-ray absorption characteristics are higher. Therefore, the S/N is higher. FIG. 11 is a diagram illustrating a table defining relationships between body thicknesses and target S/N's based on the X-ray absorption characteristics. In table LUT9, illustrated in FIG. 11, the target S/N is lower as the X-ray absorption characteristics are lower, and as the body thickness is larger. Further, the absorbed X-ray energy differs depending on the kind of a scintillator used in the radiation detector 5. For example, in the case that scintillator is CsI (cesium iodide), GOS (gadolinium oxide sulfur) and a-Se (amorphous selenium), the absorption amount increases as the X-ray energy is lower in a tube voltage range of general radiography (60 kV or higher). Therefore, the S/N is higher. FIG. 12 is a diagram illustrating a table defining relationships between body thicknesses and target S/N's based on X-ray energy with respect to the kind of a scintillator. In table LUT10 illustrated in FIG. 12, the target S/N is lower as the X-ray energy is higher, and as the body thickness is larger.

Figure 13:
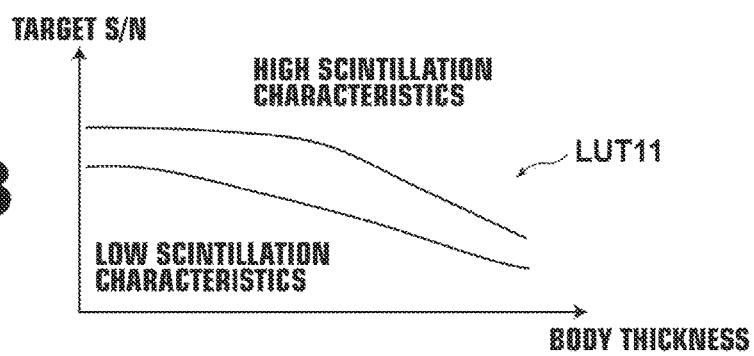
FIG. 13 is a diagram illustrating a table defining relationships between body thicknesses and target S/N's based on the scintillation characteristics of a radiation detector.

Regarding the scintillation characteristics, the obtainable signal value is higher as the scintillation amount is larger, and the S/N is higher. FIG. 13 is a diagram illustrating a table defining relationships between body thicknesses and target S/N's based on the scintillation characteristics. In table LUT11, illustrated in FIG. 13, the S/N is lower as the scintillation characteristics are lower, and as the body thickness is larger.

Regarding the film thickness of the scintillator of the radiation detector 5, the scintillation amount is larger as the film thickness is larger. Therefore, the signal value is larger, and the S/N is higher. In this case, a table defining relationships between body thicknesses and target S/N's based on the film thickness is the same as table LUT8, illustrated in FIG. 10.

The target S/N setting unit 34 sets a target S/N of radiographic image G0 based on information about at least one of the radiography condition, the subject condition and the detector characteristics, obtained by the first information obtainment unit 32, and the body thickness information, obtained by the second information obtainment unit 33, by referring to tables LUT1 through LUT11, stored in the storage 23.

Here, FIG. 3 through FIG. 13 show tables defining relationships between body thicknesses and target SN's based on each element included in the radiography condition, the subject condition and the detector characteristics. In actual cases, the target S/N setting unit 34 sets a final target S/N by integrating target S/N's that are set with reference to tables LUT1 through LUT11 about respective elements included in the radiography condition, the subject condition and the detector characteristics obtained by the first information obtainment unit 32. Therefore, a target S/N that is set with reference to the table about one of the elements is changed in some cases by being integrated with a target S/N that is set with reference to a table about another element. For example, the target S/N that is set with reference table LUT1 based on a dose is changed in some cases by being integrated with a target S/N that is set with reference to table LUT11 based on the scintillation characteristics.

The image processing unit 35 performs noise removal processing on radiographic image G0, and corrects the S/N of radiographic image G0 to a target S/N. At the time of noise removal processing, first, the image processing unit 35 separates a noise component from radiographic image G0. For example, the image processing unit 35 separates noise component Gn of radiographic image G0 by blurring radiographic image G0 by a low-pass filter, and by subtracting blurred radiographic image Gus from radiographic image G0. Further, the image processing unit 35 generates processed radiographic image G1 by suppressing noise component Gn by multiplying noise component Gn by a coefficient of less than 1, and by adding suppressed noise component Gn to blurred radiographic image Gus. The image processing unit 35 changes the degree of noise removal by setting, based on the target S/N, the coefficient by which noise component Gn is multiplied, and corrects the S/N of radiographic image G0 to the target S/N. At this time, the S/N of radiographic image G0 is corrected to the target S/N by increasing the degree of noise removal by lowering the coefficient as the body thickness is larger.

Here, the noise component of radiographic image G0 may be removed by blurring radiographic image G0 by a low-pass filter. At this time, the image processing unit 35 changes the degree of noise removal by setting, based on the target S/N, the size of the low-pass filter, and corrects the S/N of radiographic image G0 to the target S/N. At this time, the S/N of radiographic image G0 is corrected to the target S/N by increasing the degree of blur as the body thickness is larger.

Further, the image processing unit 35 may perform noise removal processing by generating band images representing frequency components for plural frequency bands by performing frequency decomposition on radiographic image G0, and by suppressing a band image of a frequency band corresponding to noise by multiplying the band image of the frequency band corresponding to noise by a coefficient of less than 1. In this case, processed radiographic image G1 is obtained by performing frequency synthesis on the band image multiplied by the coefficient and band images of the other frequency bands. Here, the image processing unit 35 changes the degree of noise removal by setting, based on the target S/N, the coefficient by which the band image of the frequency band corresponding to the noise is multiplied.

Here, processing for suppressing a band image of a frequency band corresponding to noise may be smoothing processing. In this case, as disclosed in Japanese Unexamined Patent Publication No. 2002-133410, noise included in radiographic image G0 may be removed without deterioration of edge components in radiographic image G0 by detecting an edge direction of a region of interest, which is a target of processing, in the band image of the frequency band corresponding to noise, and by performing smoothing processing along the edge direction.

Further, the image processing unit 35 performs contrast adjustment processing on radiographic image G0. In the present embodiment, the contrast adjustment processing is performed based on the degree of noise removal. Specifically, the contrast adjustment processing is performed in such a manner that contrast is higher as the degree of noise removal is higher.

Here, in the case that the noise component has been separated from radiographic image G0, as described above, the image processing unit 35 performs contrast adjustment processing on blurred radiographic image Gus. In this case, processed radiographic image G1 is obtained by adding suppressed noise component G1 to radiographic image Gus on which contrast adjustment processing has been performed. Further, in the case that noise removal processing has been performed by blurring radiographic image G0, contrast adjustment processing should be performed on radiographic image G0 on which noise removal processing has been performed. Further, in the case that frequency decomposition has been performed on radiographic image G0, processed radiographic image G1 should be obtained by performing contrast adjustment processing on a band image of a low frequency band including density information about radiographic image G0, and by performing frequency synthesis on band images including the band image on which contrast adjustment processing has been performed and a band image on which noise removal processing has been performed.

Here, the contrast of radiographic image G0 varies also based on at least one of the radiography condition, the subject condition and the detector characteristics and the body thickness information. For example, as X-ray energy is higher, the ratio of scattered radiation, which is scattered by subject M, to X-rays that pass through subject M is higher than the ratio of primary radiation, which passes through subject M without scatter, to the X-rays that pass through subject M, and the contrast of radiographic image G0 becomes lower. Further, regarding the grid, if no grid is used., the ratio of scattered radiation to the primary radiation increases, and the contrast becomes lower. Further, regarding material constituting the grid, the transmittance of primary radiation in the case that the interspace material is fiber is higher than the transmittance of primary radiation in the case that the interspace material is aluminum. Further, in a region such as an abdomen, hand and foot, which includes a small amount of structure, and a region such as a hand and foot, the thickness of which is small, contrast is low. Further, in a breast, a difference in X-ray absorption between a mammary gland and a fat is small. Therefore, contrast is low. Regarding the sharpness of the radiation detector 5, if the sharpness of a low frequency is high, contrast is high. Therefore, the image processing unit 35 may set the contrast adjustment amount based on at least one of the radiography condition, the subject condition and the detector characteristics and the body thickness information.

Figure 14:
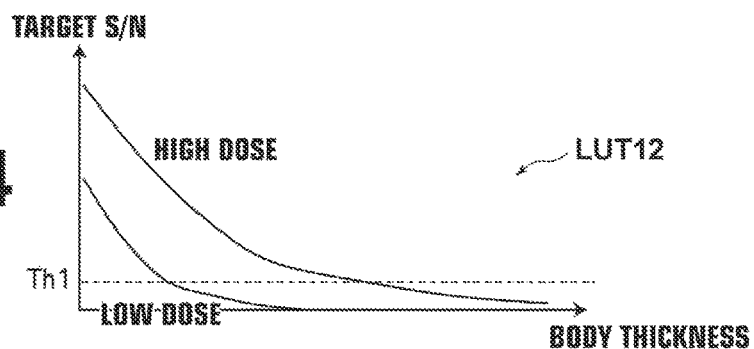
FIG. 14 is a diagram illustrating a table defining relationships between body thicknesses and signal values based on a dose.

Here, in the case that the body thickness is large, the dose of X-ray reaching the radiation detector 5 is small. Therefore, the signal value of each pixel in radiographic image G0 becomes small. In this case, even if the contrast is increased, the radiographic image does not become easily observable. On the contrary, noise becomes noticeable. Therefore, the image quality of the radiographic image becomes lower. For example, as illustrated in FIG. 14, in table LUT12 defining relationships between body thicknesses and signal values (pixel values) S based on a dose, if the pixel value becomes less than or equal to threshold Th1, even if the contrast is increased, the image quality of the radiographic image deteriorates. In this case, on the contrary, the image quality of the radiographic image improves by lowering the contrast. Therefore, for example, the image processing unit 35 may calculate an average value of pixel values of radiographic image G0, as a signal value of radiographic image G0, and refer to table LUT12, illustrated in FIG. 14. If the signal value is less than or equal to threshold Th1, the image processing unit 35 may perform contrast adjustment processing in such a manner to lower the contrast.

Here, the image processing unit 35 may perform, on radiographic image G0, other kinds of image processing, such as sharpness emphasis processing and density adjustment processing, in addition to the noise removal processing and the contrast adjustment processing. In the present embodiment, the image processing unit 35 obtains processed radiographic image G1 by performing these kinds of processing.

Next, processing performed in the present embodiment will be described. FIG. 15 is a flow chart showing processing performed in the present embodiment. Radiography is performed on subject M, and the image obtainment unit 31 of the computer 2 obtains a radiographic image (step ST1). The first information obtainment unit 32 obtains information about at least one of a radiography condition, a subject condition and detector characteristics obtainment of information such as radiography condition: step ST2). Further, the second information obtainment unit 33 obtains body thickness information about subject M (step ST3). The target S/N setting unit 34 sets a target S/N of the radiographic image based on the body thickness information and information about at least one of the radiography condition, the subject condition and the detector characteristics (step ST4). Further, the image processing unit 35 generates processed radiographic image G1 by performing, on radiographic image G0, image processing including noise removal processing and contrast adjustment processing to make the S/N of radiographic image G0 to target S/N (step ST5), and processing ends. Processed radiographic image G1 is provided for diagnosis by being displayed on the display unit 6.

As described above, in the present embodiment, the target S/N of radiographic image G0 is set based on the body thickness information and information about at least one of the radiography condition, the subject condition and the detector characteristics. Further, the S/N of radiographic image G0 is corrected to the target S/N by performing noise removal processing for removing noise included in radiographic image G0. Therefore, high-image-quality processed radiographic image G1 having an appropriate S/N based on at least one of the radiography condition, the subject condition and the detector characteristics and the body thickness is obtainable.

Further, higher-image-quality processed radiographic image G1 having appropriate contrast is obtainable by further performing contrast correction processing for correcting the contrast of radiographic image G0.

In the above embodiments, the first information obtainment unit 32 obtains information about at least one of a radiography condition, a subject condition and detector characteristics. Alternatively, the first information obtainment unit 32 may obtain information about the radiography condition, or the subject condition or the detector characteristics. In this case, the first information obtainment unit 32 may obtain information only about an element constituting the radiography condition, an element constituting the subject condition and/or an element constituting the detector characteristics. In the case that information about plural elements has been obtained about the radiography condition, the subject condition or the detector characteristics has been obtained, the target S/N setting unit 34 sets a final target S/N by integrating target S/N's that are set for the elements, respectively, with reference to tables LUTs. In the case that information about an element constituting the radiography condition, an element constituting the subject condition or an element constituting the detector characteristics has been obtained, the target S/N setting unit 34 sets the target S/N with reference to table LUT about the obtained element.

Next, the action and effect of the present embodiment will be described.

A higher-image-quality radiographic image having appropriate contrast is obtainable further by performing contrast adjustment processing on the radiographic image.

It is possible to efficiently perform noise removal processing by separating a noise component from a radiographic image, and by performing noise removal processing by suppressing the separated noise component. Further, it is possible to efficiently perform contrast adjustment processing by performing contrast adjustment processing by adjusting the contrast of the radiographic image from which the noise component has been separated.

It is possible to efficiently perform noise removal processing by generating band images of plural frequency bands by decomposing a radiographic image into plural frequency bands, and by performing noise removal processing by suppressing a band image of a frequency band corresponding to noise. Further, it is possible to efficiently perform contrast adjustment processing by performing contrast adjustment processing by adjusting the contrast of a band image of a frequency band corresponding to density information about the radiographic image.

What is claimed is:

1. A radiographic image processing apparatus comprising:
    an image obtainment unit that obtains a radiographic image radiographed by irradiating a subject with radiation and by detecting the radiation passed through the subject by a radiation detector;
    a first information obtainment unit that obtains information about at least one of a radiography condition during radiography of the subject, a subject condition and detector characteristics, which are characteristics of the radiation detector;
    a second information obtainment unit that obtains body thickness information representing the body thickness of the subject;
    a target S/N setting unit that sets a target S/N of the radiographic image based on the body thickness information and information about at least one of the radiography condition, the subject condition and the detector characteristics; and
    an image processing unit that corrects the S/N of the radiographic image to the target S/N by performing, on the radiographic image, noise removal processing for removing noise.

2. The radiographic image processing apparatus, as defined in claim 1, wherein the image processing unit increases the degree of removal of noise included in the radiographic image as the body thickness is larger.

3. The radiographic image processing apparatus, as defined in claim 2, wherein the image processing unit increases the degree of removal of the noise by increasing the degree of a blur of the radiographic image as the body thickness is larger.

4. The radiographic image processing apparatus, as defined in claim 1, wherein the target S/N setting unit sets the target S/N lower as the body thickness is larger.

5. The radiographic image processing apparatus, as defined in claim 1, wherein the image processing unit further performs contrast adjustment processing on the radiographic image.

6. The radiographic image processing apparatus, as defined in claim 5, wherein the image processing unit adjusts the contrast of the radiographic image based on the degree of removal of the noise.

7. The radiographic image processing apparatus, as defined in claim 1, wherein the image processing unit performs the noise removal processing by separating a noise component included in the radiographic image from the radiographic image, and by suppressing the separated noise component.

8. The radiographic image processing apparatus, as defined in claim 1, wherein the image processing unit performs the noise removal processing by generating band images of a plurality of frequency bands by decomposing the radiographic image into the plurality of frequency bands, and by suppressing a band image of a frequency band corresponding to the noise.

9. The radiographic image processing apparatus, as defined in claim 5, wherein the image processing unit performs the noise removal processing by separating a noise component included in the radiographic image from the radiographic image, and by suppressing the separated noise component, and performs the contrast adjustment processing by adjusting the contrast of the radiographic image from which the noise component has been separated.

10. The radiographic image processing apparatus, as defined in claim 5, wherein the image processing unit performs the noise removal processing by generating band images of a plurality of frequency bands by decomposing the radiographic image into the plurality of frequency bands, and by suppressing a band image of a frequency band corresponding to the noise, and performs the contrast adjustment processing by adjusting the contrast of a band image of a frequency band corresponding to density information about the radiographic image.

11. A radiographic image processing method comprising:
    obtaining a radiographic image radiographed by irradiating a subject with radiation and by detecting the radiation passed through the subject by a radiation detector;
    obtaining information about at least one of a radiography condition during radiography of the subject, a subject condition and detector characteristics, which are characteristics of the radiation detector;

obtaining body thickness information representing the body thickness of the subject;

setting a target S/N of the radiographic image based on the body thickness information and information about at least one of the radiography condition, the subject condition and the detector characteristics; and correcting the S/N of the radiographic image to the target S/N by performing, on the radiographic image, noise removal processing for removing noise.

12. A non-transitory recording medium storing therein a radiographic image processing program that causes a computer to execute the procedures of:

obtaining a radiographic image radiographed by irradiating a subject with radiation and by detecting the radiation passed through the subject by a radiation detector;

obtaining information about at least one of a radiography condition during radiography of the subject, a subject condition and detector characteristics, which are characteristics of the radiation detector;

obtaining body thickness information representing the body thickness of the subject;

setting a target S/N of the radiographic image based on the body thickness information and information about at least one of the radiography condition, the subject condition and the detector characteristics; and correcting the S/N of the radiographic image to the target S/N by performing, on the radiographic image, noise removal processing for removing noise.

* * * * *